United States
Lancee et al.

[11] 4,016,862
[45] Apr. 12, 1977

[54] ECHOSCOPE FOR EXAMINATION OF OBJECTS

[76] Inventors: Charles T. Lancee, Westeinde 17, Waarder; Gerardus van Zwieten, Klompenmakerij 42, Smitshoek, both of Netherlands

[22] Filed: June 16, 1975

[21] Appl. No.: 587,385

Related U.S. Application Data

[63] Continuation-in-part of Ser. No. 428,769, Dec. 27, 1973, abandoned.

[30] Foreign Application Priority Data

Dec. 28, 1972 Netherlands ............... 7217703

[52] U.S. Cl. .................... 128/2 V; 128/2.05 Z; 73/67.8 R; 330/29; 330/134
[51] Int. Cl.² ..................... A61B 10/00
[58] Field of Search ......... 128/2 V, 2.05 Z, 2.06 B; 73/67.7, 67.8, 67.9; 330/29, 127, 134

[56] References Cited

UNITED STATES PATENTS

| | | | |
|---|---|---|---|
| 3,309,914 | 3/1967 | Weighart | 73/67.9 |
| 3,348,410 | 10/1967 | Henry | 73/67.8 |
| 3,349,609 | 10/1967 | Nikonov et al. | 73/67.9 |
| 3,451,006 | 6/1969 | Grangaard | 128/2.06 B |
| 3,572,324 | 3/1971 | Petersen | 128/2.06 B |
| 3,606,879 | 9/1971 | Estes | 128/2.05 Z |
| 3,789,833 | 2/1974 | Bom | 128/2 V |
| 3,883,815 | 5/1975 | Grundy | 330/29 |

OTHER PUBLICATIONS

Crawford, et al., "Trans. of Ultrasound Through Living Human Thorax," IRE Trans. on Med. Elec., Sept. 1959, pp. 141–146.

*Primary Examiner*—Robert W. Michell
*Assistant Examiner*—Lee S. Cohen

[57] ABSTRACT

An echoscope for examination of objects with the aid of ultrasonic pulses, comprising at least one electroacoustic element for transmitting and receiving ultrasonic pulses during a transmission-reception period divided into n consecutive time intervals. The ultrasonic pulses are sent to the objects to be examined and are reflected therefrom. The echo signals supplied by the receiving element are amplified by an amplifier with time-dependent gain control. The gain control is brought about by a control voltage generator which supplies a control voltage to said amplifier for determining its signal gain as a function of time. Adjusting means for the control voltage generator are provided to make it possible to change the magnitude of the control voltage in the time intervals as a function of time. The apparatus also comprises a device for visually displaying the echo signals received during each transmission-reception period.

20 Claims, 6 Drawing Figures

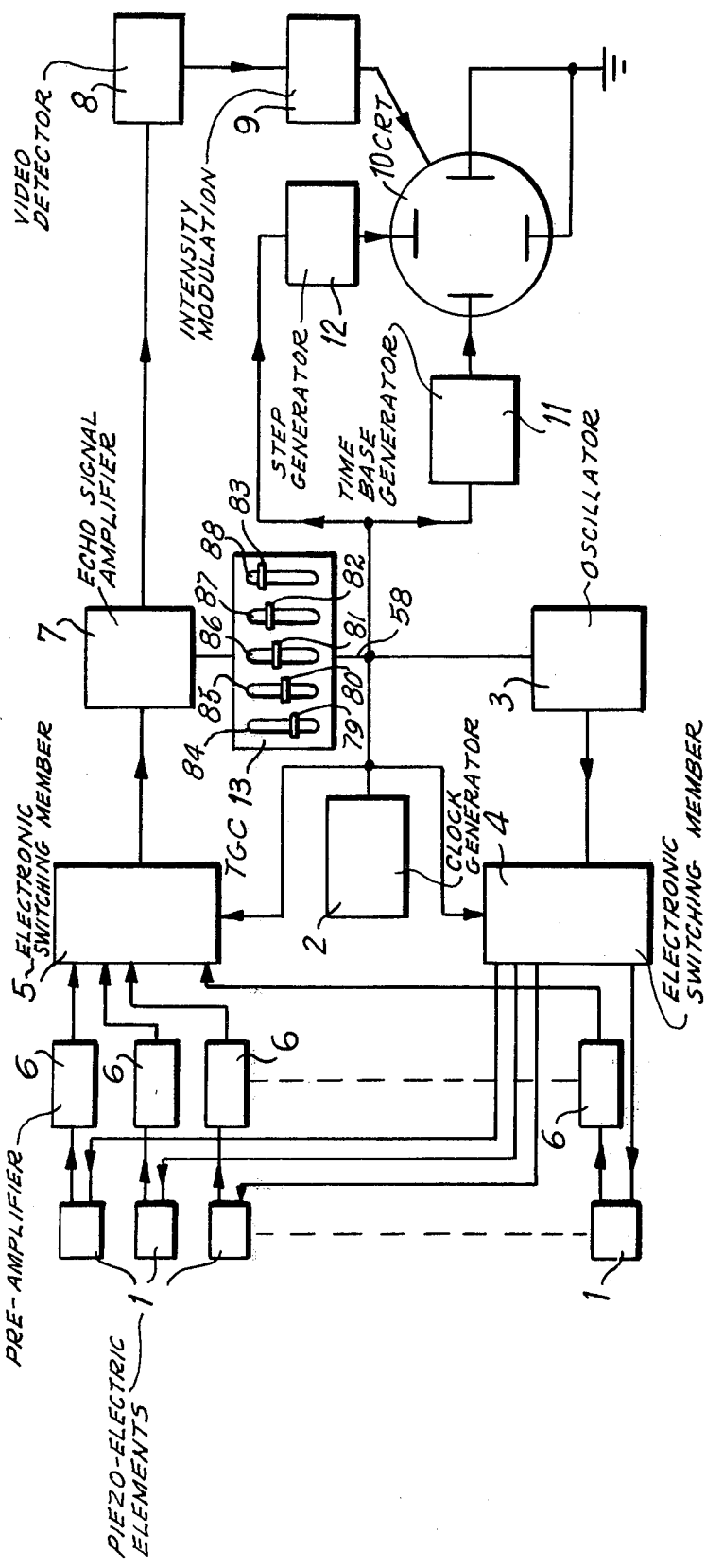

ECHOSCOPE FOR EXAMINATION OF OBJECTS

BACKGROUND OF THE INVENTION

This application is a continuation-in-part of copending application Ser. No. 428,769 filed Dec. 27, 1973 now abandoned.

Ultrasound is used for medical-diagnostic purposes as well as for non-destructive invenstigation of materials. An ultrasound source intermittently transmits ultrasonic waves of short duration which are directed to the object to be examined. In medical diagnoses, this object may be, for instance, the heart, the eyes, the abdomen or the brains of a patient. Reflection of the ultrasound penetrated into the human body occurs in places where the acoustic impedance is subject to changes, for instance at the interfaces in the tissues. By "acoustic impedance" is to be understood here the product of the density of the object examined, and the velocity of propagation of the ultrasound.

The receiving element converts the reflected waves into an electric echo signal which, after it has been amplified, is displayed on a screen. Within each transmission-reception period echoes are displayed, which taken together form an echogram.

The visual presentation of the echogram can be realized in various ways. When displayed in A-mode, the echoes are presented on a screen as deflections perpendicular to a time axis which indicates the time of reception of the echoes.

When displayed in B-mode, the echo is presented on the screen as a spot whose brightness depends on the strength of the echo signal. As the strength of the echo received to a great extent depends, for instance, on the length and the nature of the path of the sound, it is usually possible to vary the gain with time. In this way, differences in strength of echo signals with different traveling times can be compensated for ("Time gain compensation"). A device for time gain compensation is well-known per se and described for example in Feigenbaum's book "Echocardiography", Lea and Febiger, Philadelphia 1972, page 21.

With a known echoscope of the type indicated in the above and which is applicable in, for instance, cardiologic examination, a control voltage generator is present for controlling the gain.

By means of four dials it is possible to control the gain as a function of time. This will be illustrated with the aid of the graph in FIG. 1. In it the time readings are plotted on the abscissa and the amplification factor on the ordinate.

A first dial is set at the initial gain $G_n$ prevailing during a first time interval $o$ to $t_1$ ('near gain') of the transmission-reception period. A second dial is set at the time $t_1$ ('depth compensation'), i.e. the duration of the first time interval.

In a second time interval $t_1$ to $t_2$ the gain varies with time. With a third dial the slope of the gain curve in this interval can be varied between $o$ and a positive value ('rate'). Finally, with a fourth dial the gain $G_c$ in the last interval can be set ('coarse gain').

This known echoscope has the disadvantage that the gain, as a function of time, is difficult to control. When for instance with the aid of the first dial the 'near gain' $G_n$ in the first time interval $o-t_1$ is set to a higher or lower value, also the gain curve in the second time interval is shifted upwards or downwards, respectively, and the duration of this second time interval is shortened or lengthened correspondingly. When, for instance, the 'near gain' $G_n$ is reduced the sloping part of the gain curve will come down, as a result of which the second time interval will be increased. This is shown in FIG. 1 with the gain curve indicated with a broken line. But if the gain in the second time interval is to be maintained at the original level, this is only possible by shortening the first time interval with the aid of the second dial.

If, however, the duration of the second time interval is to be maintained, this can be done by increasing the slope $\alpha$ and/or by reducing the 'coarse gain' $G_c$. If the slope $\alpha$ must not be changed, then the original duration of the second time interval can only be maintained by reducing $G_c$.

Changing the 'coarse gain' $G_c$ for instance by decreasing it, will cause the second time interval to be reduced. If this should be undesirable, then the time $t_1$ must be advanced. This is possible by reducing the slope $\alpha$. However, if the slope is to remain the same, then the duration of the second time interval can only be maintained by reducing the 'near gain' $G_n$.

In the way described above, the duration of the second time interval is reduced to its original value, but its position along the time axis has been shifted. The times $t_1$ and $t_2$ are advanced to the same extent. If both the position and the duration of the second time interval are to be maintained, as will generally be necessary, this can be effected only by bringing the entire gain curve to a lower level.

The same problems are met if $t_1$ and $\alpha$ are to be changed. In diagnostic examination the most suitable gain curve must always be re-adapted to each individual case, so that all four setting parameters ($G_n$, t, $\alpha$, and $G_c$) may be changed. It is evident that finding the correct setting will then be very difficult.

Furthermore, a device is known for generating a voltage as an arbitrary function of time. The function is approximated by a staircase wave form by sequentially connecting a number of precision resistors to a reference voltage. The staircase waveform is integrated to produce a linear segment curve (H. Schmid: "Sequential analog-digital computer", Proc. of the fall joint computer conference, Las Vegas, Nevada, Nov. 1965, chapter "arbitrary function generation", pp. 915–928). However, for each function to be generated a different set of resistors is needed.

From U.S. Pat. No. 3,033,029 an echograph for ultrasonic inspection of objects in A-mode is known which comprises an amplifier and a gain compensator to produce a substantially constant echo signal throughout the distance traversed by the ultrasound in the object. To that end for any given object to be tested the characteristic curve of the received signal amplitude is determined as a function of the distance travelled by the ultrasonic pulse. Thereafter a voltage in staircase waveform is generated and after integration of this voltage it is applied to a gain control circuit. Voltage output variations which are a function of penetration depth are thereby eliminated.

With this known echograph it is only possible to vary the slope of the gain curve in a certain time interval by the adjustment of a set of new voltages which produce a staircase waveform approximating the desired slope. This change of slope, even in one single time interval, requires readjustment of more than one parameter.

The echoscope indicated in the abstract shows the improvement of the control voltage generator being provided with a) at least two adjustable voltage sources, each of which cooperates with one of the adjusting means for arbitrarily setting the voltages ($e_i$, $e_k$) of said sources prevailing at the corresponding interval points of time ($t_i$ and $t_k$ respectively) between a minimum and a maximum value; b) a differential amplifier for each of the time intervals, the inputs of a differential amplifier for a certain time interval being connected to the adjustable voltage sources for the interval points of time separating said time interval; c) an integrator connectable to the output of said differential amplifier to integrate the output voltage of said differential amplifier during the respective time interval, the integrator time constant RC being equal to the duration of said time interval; d) setting means for setting the output voltage of the integrator at the beginning time $t_b$ of the integration ($t_b=t_k$) to the voltage reached at the ending time ($t_e$) of the preceding integration ($t_e=t_i$), so that the output voltage u(t) of the integrator is given by $$u(t) = \frac{-1}{RC} \int_{t_e}^{t} (e_e - e_b)dt - u(t_b), \text{ for } t_b < t < t_e$$

where $RC=t_e - t_b$ and $u(t_b) = e_b$, so that $u(t_e) = e_e$ and where $e_b$ and $e_e$ are the setting voltages applied to the differential amplifier, at the beginning and the end of the integration respectively.

With "electro-acoustic element" is meant an element which may convert an electric signal into an acoustic signal of ultrasonic frequency and vice versa. By "at least one electro-acoustic element" is meant that there is either at least a single element for both transmission and reception or at least one element for transmission and one for reception.

Instead of the four parameters mentioned above, viz. $G_n$, $t_1$, and $G_c$ the present invention provides, as setting parameters, the gains at at least two different interval points of time. As a result, the setting of the gain curve desired becomes more flexible and more direct, i.e. a wider choice of curve shape is possible, and the interdependence of the setting parameters will be smaller than with the known echoscope. This also leads to a simpler and more rapid setting of the desired gain curve. Changing the gain at one of the interval points of time will only influence the gain curve in the two consecutive time intervals separated by the respective interval point of time. Outside these intervals the gain curve remains unchanged.

Choosing two successive intervals points of time for varying the gain will allow influencing the gain curve in not more than three consecutive time intervals.

Choosing two non-successive interval points of time for varying the gain will allow influencing the gain curve in not more than four time intervals.

Not only the gain at various interval points of time but also these times themselves are variable.

The integrator serves as function generator which determines the variation with time, of the gain between the interval points of time. In principle, an integrator may be present for each time interval, provided that the initial voltage of an integrator is equal to the end voltage of the integrator for the preceding time interval.

A simpler solution is obtained, however, with a construction wherein said setting means comprises a switching unit provided with a number of switches, one contact of each of said switches being connected to the output of a differential amplifier, the other contacts of said switches being commonly connected to the input of the integrator, and a timing generator controlling the switching unit for successively closing the switches at the interval points of time.

The switching unit is preferably provided with electronic switches.

A very suitable embodiment of the echoscope according to the invention has the feature that the voltage sources are formed by potentiometers with linear reading scale, more particularly a sliding potentiometer, which is connected to a source of constant d.c. voltage. This potentiometer is not purely equivalent here to a potentiometer without linear reading scale. With the apparatus, according to the invention, potentiometers with a linear reading scale have the particular advantage that their position, moreover, gives the operator a picture of the gain curve. As a result the operator can immediately observe the effect produced on the gain curve of a variation in the setting, so that this curve need not be displayed on a screen, as is the usual case with other known apparatuses. This advantage could not be obtained if, with the conventional apparatus, use was made of potentiometers with a linear reading scale.

In another embodiment of the echoscope, according to the invention, the amplifier is an electronic amplifier to which there is connected a variable resistor for setting the gain. The afore-mentioned resistor is provided with means for electrically setting the resistance value, these means, furthermore, are connected to the output of the control voltage generator.

The resistor is preferably formed by an electronic resistor for which a field-effect transistor is well suited.

A suitable form of amplifier is a wideband video amplifier with differential input and output.

The invention will be elucidated with reference to the embodiment illustrated in the accompanying drawing.

BRIEF DESCRIPTION OF THE DRAWING

FIG. 6 schematically shows an echoscope according to the present invention for diagnostic purposes.

DESCRIPTION OF THE PREFERRED EMBODIMENTS

Figure 1:
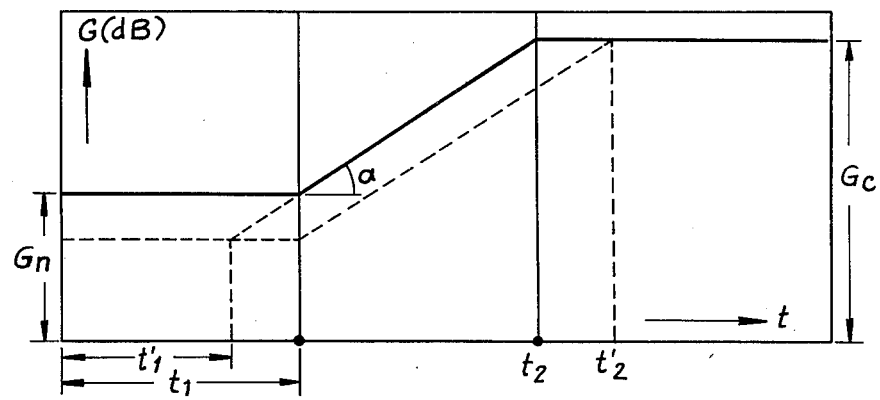
FIG. 1 shows a gain curve of a known echoscope.

FIG. 6 shows a number of piezo-electric elements 1 arranged in a row. The elements 1 are supported in a transducer of which the acoustically active surface is to be placed on the body of a patient to be examined. The acoustically active surface transfers the ultrasonic vibrations of the elements to the patient's body.

Each of the elements 1 serve as transmitter and receiver of ultrasound. The ultrasound pulses emitted by a certain element are reflected at the interfaces in the tissues. The reflected ultrasound is converted into an electric echo signal to be displayed on a cathode ray tube.

The elements 1 have parallel axes of radiation lying in a plane adapted to intersect the body part being examined along a predetermined cross-section. The elements are repeatedly excited at such a high repetition frequency that an instantaneous two-dimensional image of said cross-section is observed on the screen of the cathode ray tube.

A more detailed description of such an echoscope is found in U.S. Pat. No. 3,789,833.

The excitation of the piezo-electric elements is controlled by a clock generator 2 which also controls an oscillator 3 and electronic switching members 4 and 5. The electronic switching member 4 successively connects all piezo-electric elements 1 to the oscillator 3 which generates the oscillations for the excitation of the elements.

Each element 1 is connected to a pre-amplifier 6 which amplifies the echo signals obtained upon reception of reflected ultrasound. The outputs of the pre-amplifiers 6 are, through the intermediary of the electronic switching member 5, successively connected to a common echo signal amplifier 7. The gain of amplifier 7 is determined by a time-gain compensating means 13 which is also under the control of clock generator 2. The amplified echo signals are then supplied to a video detector 8 and a device 9 for producing an intensity modulation of the cathode ray by means of the intensity-control electrode of the cathode ray tube 10.

The clock generator 2 also controls a time base generator 11 and a step generator 12 which are connected to the horizontal and vertical deflecting plates of cathode ray tube 10 respectively. As more fully described in U.S. Pat. No. 3,789,833, the echo signals originating from a particular cross-section of the body are displayed on the cathode ray tube screen in a coordinate system wherein one coordinate represents the position of each piezo-electric element in the row of elements, and another coordinate represents the time of reception of the echo signals.

Figure 2:
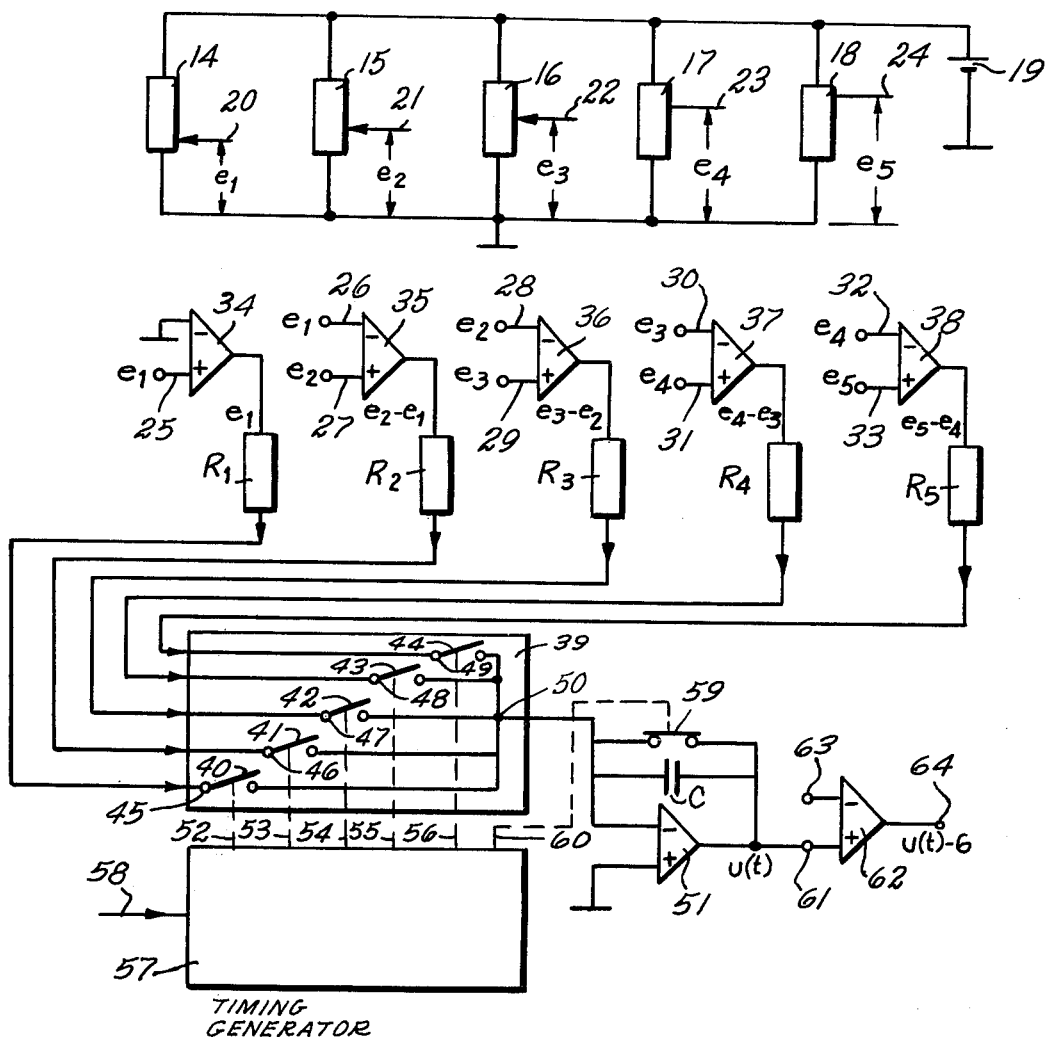
FIG. 2 is a diagrammatic representation of a control voltage generator for an amplifier according to the invention.

The time-gain compensating means 13 comprises a control voltage generator which is shown in more detail in FIG. 2.

In FIG. 2 the numerals 14 to 18 refer to a number of sliding potentiometers which are connected to a source 19 supplying a d.c. voltage of 6V. The sliding contacts 20 to 24 of the sliding potentiometers are connected to the inputs 25 to 33 of differential amplifiers 34 to 38. The outputs of the differential amplifiers are connected to a schematically shown switching unit 39 through resistors $R_1$ to $R_5$. Switching unit 39 contains a number of switches 40-44. Their contacts 45-49 are connected to resistors $R_1$ to $R_5$. The remaining contacts are connected to a common terminal 50, which is connected to an integrator 51 with capacitor C. Switches 40-44 are semi-conductor switches which, as schematically indicated by dash lines 52-56, are controlled by a timing generator 57. During each transmission-reception period timing generator 57 produces a sequence of timing signals which initiate switches 40-44 to close at the interval points of time. Switch 40 connects the integrator 51 to the contact 45 during a first interval $o$ to $t_1$ of the transmission-reception period; during a subsequent second interval $t_1$ to $t_2$ it is connected to the resistor $R_2$; during a third interval $t_2$ to $t_3$ it is connected to resistor $R_3$; during a fourth interval $t_3$ to $t_4$ it is connected to resistor $R_4$ and during a fifth interval $t_4$ to $t_5$ it is connected to resistor $R_5$.

Timing generator 57 is connected to clock generator 2 through lead 58, as shown in FIG. 6. Each time the clock generator 2 starts a new transmission-reception period, timing generator 57 initiates switching unit 39 to connect integrator 51 to contact 45. For timing generator 57 any timing generator may be used capable of sequentially supplying timing signals at the interval points of time. The instants at which the timing signals are supplied should preferably be variable. For example, FIG. 4 of the above-cited article of H. Schmid shows a control unit with a timing generator and a switching unit of the kind which may be applied to the control voltage generator of FIG. 2 of the present application. Timing generator 57 may also be made up of an m-bit counter connected to a code convertor (decoder) which supplies the required timing signals at the interval points of time to close switches 40-44 through appropriate switch drivers.

Parallel to the capacitor C is a switch 59. It is also under control of timing generator 57, as schematically indicated by the dash line 60. The output voltage $u(t)$ of the integrator 51 is applied to the input 61 of a differential amplifier 62. To the other input 63 of the amplifier, a voltage of +6 Volts is applied. The voltage at the output 64 of the differential amplifier 62 will then be $C(t) = u(t) - 6$ Volts.

Figure 3:
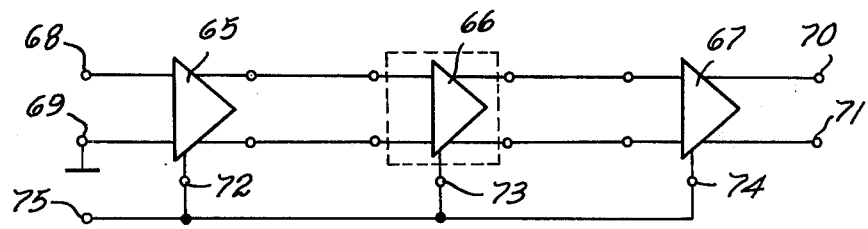
FIG. 3 is a schematic diagram of a three-stage echo signal amplifier for an apparatus according to the invention.

The output 64 is connected to the echo signal amplifier 7 of FIG. 6. This amplifier is schematically represented in FIG. 3 and consists of three identical amplifier stages 65, 66 and 67. The echo signals are fed to the inputs 68, 69 and arrive amplified at the outputs 70, 71 which are connected to a video detector 8 shown in FIG. 6. The amplifier stages 65 to 67 are provided with contacts 72, 73 and 74, respectively, through which the gain may be set. The contacts 72 to 74 are centrally connected to 75 to the output 64 of the control voltage generator represented in FIG. 2.

The three amplifiers 65 to 67 are constructed as an integrated circuit of the S 5733 type of Signetics Corporation, as described in their Preliminary Specification of August 1969.

The differential amplifier here is a wideband video amplifier with differential output. This amplifier can be connected to an external resistor for setting the gain.

Figure 4:
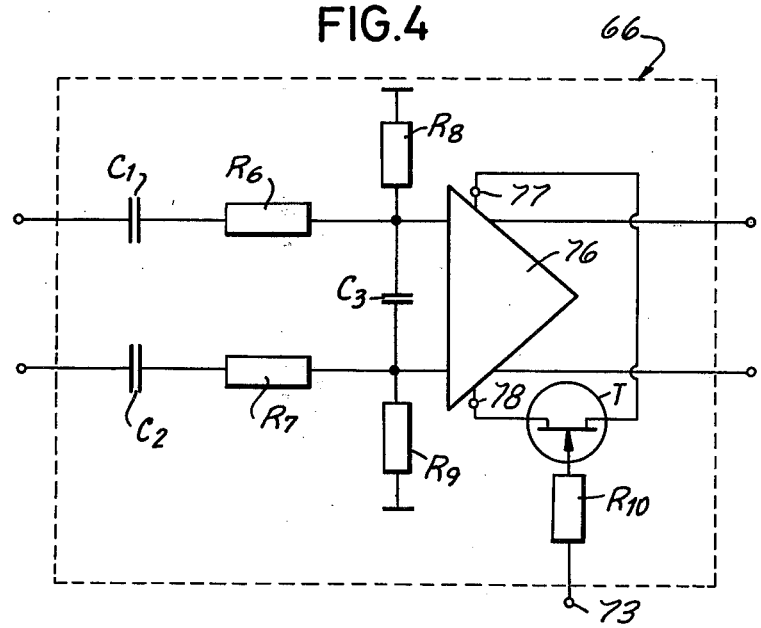
FIG. 4 represents a detail of the amplifier shown in FIG. 3.

FIG. 4 further illustrates the middle amplifier stage 66.

The actual amplifier, of the S 5733 type, is referred to by the numeral 76. Its gain can be varied in the range of 10 to 400.

In order that a minimum gain of 1 may be obtained, a 10-fold attenuation must be applied. This attenuation is realised by means of a band-pass filter for each amplifier stage. With this, it is also possible to limit the noise. For this purpose the differential amplifier 76 has at its input a symmetrical band-pass filter consisting of the resistors $R_6$ to $R_9$ and the capacitors $C_1$ to $C_3$.

Suitable values are: $R_6 = R_7 = 910\Omega$; $C_1 = C_2 = 150$ pF and $C_3 = 82$ pF.

Connected between the control inputs 77 and 78 (gain select pins) of the differential amplifier 76, is a variable electronic resistor in the form of a field-effect transistor T of the U 1898 E type made by Amelco Semiconductor, U.S.A. The control electrode of T is connected to the control input 73 through the resistor $R_{10}$ having a value of 13kΩ. This connection results in a gain range of 1 to 21.5 times per stage.

The control voltage generator described above operates as follows: The sliding potentiometers 14 to 18 are set in accordance with the desired gain curve. Together with the source 6 of constant d.c. voltage, they each form a voltage source, with the respective voltages indicated by $e_1$, $e_2$, $e_3$, $e_4$ and $e_5$. Consequently, the output voltages of the differential amplifiers 21 to 25 are $e_1$, $e_2 - e_1$, $e_3 - e_2$, $e_4 - e_3$ and $e_5 - e_4$, respectively.

The capacitor C and the resistors $R_1$ to $R_5$ are chosen so that:

$$R_1C = t_1$$
$$R_2C = t_2 - t_1$$
$$R_3C = t_3 - t_2$$
$$R_4C = t_4 - t_3$$
$$R_5C = t_5 - t_4.$$

Initially, all switches in switching unit 39 are in the open position indicated in FIG. 2 and the switch 59 is closed, so that the output voltage of the integrator is zero.

At the start of the transmission-reception period ($t = 0$), the switch 59 is opened and the switching unit 39 will under the control of timing generator 57 connect the central contact 50 with the contact 45. As a result, the integrator 51 is set into operation for a first time interval $o$ to $t_1$ of 12.5 $\mu$ sec.

Therefore, the output voltage $u(t)$ of the integrator is:

$$u(t) = \frac{-1}{R_1C} \int_0^t e_1 dt \text{ for } 0 \leq t \leq t_1,$$

so that $u(t_1) = -e_1$, with $R_1C = t_1 = 12.5$ $\mu$sec.

At time $t = t_1 = 12.5\mu$sec., the switching unit 39 connects the integrator 51 to the contact 46. The variation in the output voltage of the integrator in the interval $t_1$ to $t_2$ ($t_2 = 25\mu$sec) is then given by $$u(t) = \frac{-1}{R_2C} \int_{t_1}^t (e_2 - e_1)dt - e_1 \text{ for } t_1 \leq t \leq t_2,$$

so that, $u(t_2) = -e_2$, with $R_2C = t_2 - t_1 = 12.5\mu$sec.

Likewise, the integrator 51 is via the contacts 47, 48 and 49 connected to the differential amplifiers 36, 37 and 38 at the times $t_3 = 50\mu$sec., $t_4 = 100\mu$sec., and $t_5 = 200\mu$sec.

For the following time intervals $t_2$ to $t_3$, $t_3$ to $t_4$ and $t_4$ to $t_5$ one may write:

$$u(t) = \frac{-1}{R_3C} \int_{t_2}^t (e_3 - e_2)dt - e_2 \text{ for } t_2 \leq t \leq t_3$$

so that $u(t_3) = -e_3$, with $R_3C = t_3 - t_2 = 25\mu$sec;

$$u(t) = \frac{-1}{R_4C} \int_{t_3}^t (e_4 - e_3)dt - e_3 \text{ for } t_3 \leq t \leq t_4,$$

so that $u(t_4) = -e_4$, $R_4C = t_4 - t_3 = 50\mu$sec;

and $$u(t) = \frac{-1}{R_5C} \int_{t_4}^t (e_5 - e_4)dt - e_4 \text{ for } t_4 \leq t \leq t_5,$$

so that $u(t_5) = -e_5$, with $R_5C = t_5 - t_4 = 100\mu$sec.

For each of the five time intervals the respective control voltage follows from $C(t) = u(t) - 6$ Volts.

The control voltage $C(t)$ is applied to the control inputs 72–74 of the amplifiers 65 to 67 through the contact 75 (see FIG. 3). As the voltage $u(t)$ of the integrator 51 may range between 0 and 6 volts, the control voltage $C(t)$ varies between $C_{min.} = -6$ V, and $C_{max.} = 0V$. Within a large part of this last mentioned range the gain (in dB) increases substantially in direct proportion to the control voltage.

Figure 5:
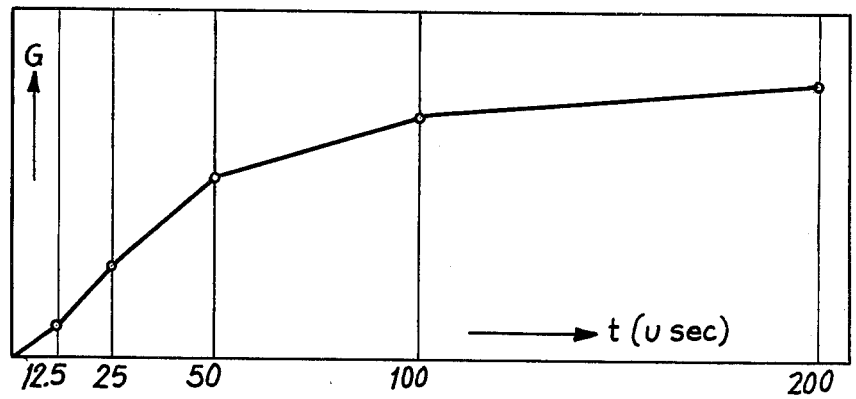
FIG. 5 illustrates a gain curve obtained with the apparatus according to the invention.

FIG. 5 shows a gain curve as obtained with the settings shown in FIG. 2 for the sliding potentiometers 14 to 18. On the abscissa are plotted the time readings, with $t = o$ indicating the beginning of a transmission-reception period. In FIG. 6 the sliding potentiometers of the time-gain compensating means 13 are shown by their adjusting knobs 79, 80, 81, 82 and 83. These knobs are slidable in vertical slits 84–88 provided in the front panel of the echo scope.

FIG. 5 shows that the settings of the sliding potentiometers 14–18 in FIG. 2 and FIG. 6 give a visual presentation of the shape of the gain curve, thus facilitating the task of the operator.

Although in FIG. 5 the gains at all five interval points of time are between the same minimum ($o$ dB) and maximum gain (80 dB), this is not essential. It is also conceivable that the gain at each interval point of time can be between a respective minimum and maximum value.

It will be clear that with the above-described echoscope not only a gain curve with a positive slope can be realised, but also a curve with one or more parts of it having a negative slope.

With the circuit shown in FIG. 4 an extremely rapid change in gain may be effected. Thus it is possible with an adapted control voltage to have the total gain of the three-stage amplifier shown in the FIGS. 3 and 4 changed from the minimum ($1x$) gain to the maximum 10,000 ($21.5^3$) gain, i.e. from 0 to 80 dB, within 5$\mu$sec.

Due to this high speed, which can be realized with the aid of a variable electronic resistor such as a field-effect transistor, it is possible to use the invention also for very short transmission-reception periods. This is of particular advantage if the ultra-sound is to cover only a short distance, as is the case with ultrasound examination of the eye.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed as new and desired to be protected by Letters Patent is set forth in the appended claims:

1. In an echoscope for examination of objects with the aid of an ultrasound beam, comprising at least one electro-acoustic element for transmitting and receiving ultrasonic pulses during a transmission-reception period; an amplifier with time-dependent gain control cooperating with the electro-acoustic element for amplifying the echo signals supplied by said element; a control voltage generator connected to said amplifier for supplying a control voltage thereto to determine the signal gain as a function of time; adjusting means in said control voltage generator for permitting changing the magnitude of the control voltage as a function of time in n consecutive time intervals of the transmission-reception period, which are bounded by the interval points of time $t_1, t_2, \ldots t_i, t_j, t_k, \ldots t_{n-1}, t_n$; and a display connected to the echo signal amplifier for the visual display of the echo signals received during each transmission-reception period, the improvement of the control voltage generator comprising a) at least two adjustable voltage sources, each of which cooperates with the adjusting means for arbitrarily setting the voltages ($e_i$, $e_j$) of said sources prevailing at the corresponding interval points of time ($t_i$ and $t_j$ respectively) between a minimum and a maximum value; b) a differential amplifier for each of the time intervals connected to the adjustable voltage sources corresponding to the interval points of time bounding said time interval; c) integrator means for supplying the control voltage to the echo signal amplifier, said integrator means cooperating with the differential amplifiers to integrate the output voltages ($e_j - e_i$) of said differential amplifiers during the respective time interval ($t_i$ to $t_j$) with an integrator time constant $(RC)_j$; and d) switching means cooperating with said integrator means for successively integrating the difference voltages ($e_j - e_i$) during consecutive time intervals ($t_j - t_i$), said time intervals ($t_j - t_i$) corresponding to the respective integrator time constants $(RC)_j$ according to the relation $$\frac{t_j - t_i}{(RC)_j} = \ldots = \frac{t_2 - t_1}{(RC)_2} = \frac{t_1}{(RC)_1},$$

with $i = 0, 1, 2, \ldots, n-1$, and $j = i+1$.

2. An echoscope according to claim 1, wherein said switching means comprises a switching unit provided with a number of switches, one contact of each of said switches being connected to the output of one of said differential amplifiers, the other contacts of said switches being commonly connected to the input of the integrator means, and timing generator means cooperating with the switching unit to successively close the switches at the interval points of time.

3. an echoscope according to claim 2, wherein said switches are electronic switches.

4. An echoscope according to claim 1, wherein said voltage sources are formed by potentiometers with linear reading scales and a source of constant D.C. voltage connected to said potentiometers.

5. An echoscope according to claim 4, wherein said potentiometers are sliding potentiometers, having juxtaposed adjusting knobs which are slidable in substantially parallel directions, so that their positions give a picture of the signal gain as a function of time.

6. An echoscope according to claim 1, an electronic amplifier with a variable resistor for setting the gain connected to said amplifier, said resistor having means for electrically setting the resistance value, and being connected to the output of said control voltage generator.

7. An echoscope according to claim 6, wherein said resistor is an electronic resistor.

8. An echoscope according to claim 7, wherein said electronic resistor is a field-effect transistor.

9. An echoscope according to claim 6, wherein said electronic amplifier is a wideband video amplifier with differential input and output.

10. An echoscope according to claim 1, wherein the control voltage generator is provided with a. $n$ voltage sources, one for each interval point of time ($\ldots, t_i, t_j, t_k, \ldots t_{n-1}, t_n$);

b. n differential amplifiers each of which is connected to one of said voltage sources;

c. common integrator means cooperating with the differential amplifiers to integrate their output voltages ($\ldots; e_j - e_i; \ldots; e_n - e_{n-1}$) during the corresponding time intervals ($\ldots; t_i$ to $t_j; \ldots t_{n-1}$ to $t_n$); and d. switching means cooperating with said common integrator means for successively connecting the outputs of the differential amplifiers to the input of the integrator means during the corresponding time intervals ($\ldots; t_i$ to $t_j; \ldots; t_{n-1}$ to $t_n$).

11. In an echoscope for examination of parts inside a human body with the aid of ultrasonic pulses, comprising an ultrasonic transducer having an acoustically active surface to be externally placed on the body of a patient; a number of electroacoustic elements supported in said transducer for transmitting and receiving ultrasonic pulses during each transmission-reception period, said transmitting elements having parallel axes of radiation lying in a plane adapted to intersect the body part being examined along a predetermined cross-section; an amplifier with time-dependent gain control cooperating with the electroacoustic elements for amplifying the echo signals supplied by the receiving elements; a control voltage generator connected to said amplifier for supplying a control voltage thereto to determine the signal gain as a function of time; adjusting means in said control voltage generator for permitting changing the magnitude of the control voltage as a function of time in n consecutive time intervals of the transmission-reception period, which are separated by the interval points of time $t_1, t_2, \ldots, t_i, t_j, t_k, \ldots, t_{n-1}, t_n$; a cathode ray tube including a screen cooperating with the echo signal amplifier; means for displaying echo signals reflected by parts of body at the predetermined cross-section and received by said elements on the screen of said cathode ray tube in a coordinate system wherein one coordinate represents the position of the transmitted ultrasound beam, and another coordinate represents the time of reception of said echo signals; and means for repeatedly exciting said electro-acoustic elements at such a repetition frequency that an instantaneous image of said cross-section is displayed on the screen of said cathode ray tube, the improvement of the control voltage generator being provided with a) at least two adjustable voltage sources, each of which cooperates with the adjusting means for arbitrarily setting the voltages ($e_i$ $e_j$) of said sources prevailing at the corresponding interval points of time ($t_i$ and $t_j$ respectively) between a minimum and a maximum value; b) a differential amplifier for each of the time intervals connected to the adjustable voltage sources for the interval points of time bounding said time interval; c) integrator means for supplying the control voltage to the echo signal amplifier, said integrator means being connectable to the outputs of said differential amplifiers to integrate the output voltages of said differential amplifiers during the respective time interval ($t_i$ to $t_j$) with an integrator time constant $(RC)_j$; and d) switching means cooperating with said integrator means for successively integrating the difference voltages ($e_j - e_i$) during consecutive time intervals ($t_j - t_i$), said time intervals ($t_j - t_i$) corresponding to the respective integrator time constant $(RC)_j$ according to the relation $$\ldots \frac{t_j - t_i}{(RC)_j} = \ldots = \frac{t_2 - t_1}{(RC)_2} = \frac{t_1}{(RC)_1},$$

with $i = 0, 1, 2, \ldots, n-1$, and $j = i+1$.

12. An echoscope according to claim 11, wherein said switching means comprises a switching unit provided with a number of switches, the one contact of each of said switches being connected to the output of one of said differential amplifiers, the other contacts of said switches being commonly connected to the input of the integrator means, and timing generator means cooperating with the switching unit to successively close the switches at the interval points of time.

13. An echoscope according to claim 12, wherein said switches are electronic switches.

14. An echoscope according to claim 11, wherein said voltage sources are formed by potentiometers with linear reading scales, and a source of constant D.C. voltage connected to said potentiometers.

15. An echoscope according to claim 14, wherein said potentiometers are sliding potentiometers, having juxtaposed adjusting knobs which are slidable in substantially parallel directions, so that their positions give a picture of the signal gain as a function of time.

16. An echoscope according to claim 11, an electronic amplifier with a variable resistor for setting the gain connected to said amplifier, said resistor having means for electrically setting the resistance value, and being connected to the output of said control voltage generator.

17. An echoscope according to claim 16, wherein said resistor is an electronic resistor.

18. An echoscope according to claim 17, wherein said electonic resistor is a field-effect transistor.

19. An echoscope according to claim 16, wherein said electronic amplifier is a wideband video amplifier with differential input and output.

20. An echoscope according to claim 11, wherein the control voltage generator is provided with a) n voltage sources, one for each interval point of time ($\ldots, t_i, t_j, t_k, \ldots t_{n-1}, t_n$); b) $n$ differential amplifiers, each of which is connected to one of said voltage sources; c) common integrator means cooperating with the differential amplifiers to integrate their output voltages ($\ldots ; t_i$ to $t_j; \ldots ; t_{n-1}$ to $t_n$); and d) switching means cooperating with said common integrator means for successively connecting the outputs of the differential amplifiers to the input of the integrtor means during the corresponding time intervals ($\ldots ; t_i$ to $t_j; \ldots ; t_{n-1}$ to $t_n$).

* * * * *